(12) United States Patent
Zsolt et al.

(10) Patent No.: US 9,012,483 B2
(45) Date of Patent: Apr. 21, 2015

(54) USE OF L-HISTIDINE AND DERIVATIVES THEREOF

(75) Inventors: Baranyai Zsolt, Debrecen (HU); Ernö Brücher, Debrecen (HU); Simona Bussi, Vercelli (IT); Alessandro Maiocchi, Monza (IT); Fulvio Uggeri, Codogno (IT)

(73) Assignee: Bracco Imaging S.p.A., Milan (IT)

( * ) Notice: Subject to any disclaimer, the term of this patent is extended or adjusted under 35 U.S.C. 154(b) by 0 days.

(21) Appl. No.: 14/235,128

(22) PCT Filed: Jul. 24, 2012

(86) PCT No.: PCT/EP2012/064489
§ 371 (c)(1),
(2), (4) Date: Jan. 27, 2014

(87) PCT Pub. No.: WO2013/017475
PCT Pub. Date: Feb. 7, 2013

(65) Prior Publication Data
US 2014/0155449 A1 Jun. 5, 2014

(30) Foreign Application Priority Data
Aug. 2, 2011 (EP) .................................... 11176262

(51) Int. Cl.
*A61K 31/415* (2006.01)
*A61K 31/28* (2006.01)
*A61K 31/4172* (2006.01)

(52) U.S. Cl.
CPC ............. *A61K 31/4172* (2013.01); *A61K 31/28* (2013.01)

(58) Field of Classification Search
CPC ............................ A61K 31/28; A61K 31/4172
USPC .......................................... 514/386, 396, 492
See application file for complete search history.

(56) References Cited

U.S. PATENT DOCUMENTS

2002/0004072 A1 1/2002 Thomas
2009/0148432 A1 6/2009 Higuchi

FOREIGN PATENT DOCUMENTS

WO 2008/066862 A2 6/2008

OTHER PUBLICATIONS

PCT international Search Report for PCT/EP2012/064489, mail date Nov. 16, 2012.
PCT Written Opinion for PCT/EP2012/064489, mail date Nov. 16, 2012.
Altun, Ersan et al., "Nephrogenic Systemic Fibrosis and Management of High-risk Patients", Academic Radiology, vol. 16, No. 7, 2009, pp. 897-905.
Broome, Dale R., "Nephrogenic systemic fibrosis associated with gadolinium based contrast agents: A summary of the medical literature reporting", European Journal of Radiology, vol. 66, 2008, pp. 230-234, www.elsevier.com/locate/ejrad.
Bussi, Simona et al., "Toxicological assessment of gadolinium release from contrast media", Experimental and Toxicologic Pathology, vol. 58, 2007, pp. 323-330, www.elsevier.de/etp.
Canavese, Caterina et al., "Gadoinium-associated nephrogenic systemic fibrosis: the need for nephrologists' awareness", JNephrol, vol. 21, 2008, pp. 324-336, www.sin-italy.org/jnonline—www.jnephrol.com.
Caravan, P. et al., "Thermodynamic Stability and Kinetic Inertness of MS-325, a New Blood Pool Agent for Magnetic Resonance Imaging", Inorganic Chemistry, vol. 40, No. 9, 2001, pp. 2170-2176.
Farling, PA et al., "Guidelines: Safety in magnetic resonance units: an update", Anaesthesia Journal of the Association of Anaesthetists of Great Britain and Ireland, vol. 65, 2010, pp. 766-770.
Gerber, Donald A. et al., "Lack of an effect of oral L-histidine on the serum cholesterol in human subjects", The American Journal of Clinical Nutrition, vol. 24, 1971, pp. 1382-1383.
Jackson, Graham E. et al., "Gadolinium (III) Complex Equilibria: The Implications for Gd (III) MRI Contrast Agents", Magnetic Resonance Medicine, vol. 16, 1990, pp. 57-66.
Krefting-Ira, Gadolinium-Based Contrast Agents (GBCAs) and the NSF Risk: Regulatory Update, FDA U.S. Food and Drug Administration, Jan. 21, 2011, www.fda.gov.
Laurent, Sophie, et al., "Stability of MRI Paramagnetic Contrast Media: A Proton Relaxometric Protocol for Transmetallation Assessment", Investigative Radiology, vol. 36, No. 2, 2001, pp. 115-122, Lippincott Williams & Wilkans, Inc.
May, Peter M. et al., "Computer Simulation of Metal-ion Equilibria in Biofluids: Models for the Low-molecular-weight Complex Distribution of Calcium(II), Magnesium(II), Manganese(II), Iron(III), Copper(II), Zinc(II), and Lead(II) Ions in Human Blood Plasma", Journal Chemical Society, Dalton Trans., 1977, pp. 588-595, www.journal homepage/Table of Contents.
Morcos, S.K., "Extracellular gadolinium contrast agents: Differences in stability", European Journal of Radiology, vol. 66, 2008, pp. 175-179, www.elsevier.com/locate/ejrad.
Sarka, L., et al., The Rates of the Exchange Reactions between [Gd(DTPA]2- and the Endogenous Ions Cu2+ and Zn2+: A Kinetic Model for the Prediction of the In Vivo Stability of [Gd(DTPA)]2-, Used as a Contrast Agent in Magnetic Resonance Imaging, Chem. Eur. J., vol. 6, No. 4, 2000, pp. 719-724, WILEY-VCH Verlag GmbH D-69451, Weinheim.
Schecter, Paul J. et al., "Failure of oral L-histidine to influence appetite or affect zinc metabolism in man: a double-blind study", The American Journal of Clinical Nutrition, vol. 32, 1979, pp. 1011-1014.

(Continued)

*Primary Examiner* — Kevin E Weddington
(74) *Attorney, Agent, or Firm* — M. Caragh Noone (57) ABSTRACT

The present invention discloses the use of L-Histidine to reduce Gadolinium accumulation into target organs, preventing its toxic effects, after administration of gadolinium based contrast agents. The invention thus, also disclose the use of L-Histidine to prevent the NSF syndrome in patients with renal functionality impairment. A kit of part is also disclosed by the use of which toxicity associated to free Gd3+, deriving from GDBCA, is prevented by oral administration of L-histidine before administration of the contrast agent. A method for the prevention of toxic metal accumulation which consists in the administration, preferably by the oral route, of L-Histidine is also disclosed. L-Histidine is preferably administered as a single oral dose comprised from 0.2-20 g.

13 Claims, 3 Drawing Sheets

(56) References Cited

OTHER PUBLICATIONS

Sitton, N. G. et al., "Kinetic investigations into teh possible cause of low serum histidine in rheumatoid arthritis", Annals of the Rheumatic Diseases, vol. 47, 1988, pp. 48-52, ard.bmj.com.

"The Handbook of Pharmaceutical Excipients", 4th edition, 2003, Pharmaceutical Press, editors Raimond C. Rowe, Paul J. Sheskey, Paul J. Weller.

Tweedle, M.F. et al., "Reaction of Gadolinium Chelates With Endogenously Available Ions", Magnetic Resonance Imaging, vol. 9, 1991, p. 409-415, Pergamon Press.

Wedeking, P. et al., "Comparison of teh Biodistribution of 153Gd-Labeled Gd(DTPA)2- , Gd(DOTA)-, and Gd(Acetate)n in Mice", Nucl. Med. Biol., vol. 15, No. 4, 1988, pp. 395-402, Pergamon Press.

First Office Action for Chinese application No. 201280038043.8, mail date Dec. 31, 2014 (English translation).

Figure 1

Panel A

Panel B

Panel A

Panel B

USE OF L-HISTIDINE AND DERIVATIVES THEREOF

CROSS-REFERENCE TO RELATED APPLICATIONS

This application is the national stage application of corresponding international application number PCT/EP 2012/064489, filed Jul. 24, 2012, which claims priority to and the benefit of European application no. 11176262.1, filed Aug. 2, 2011, all of which are hereby incorporated by reference in their entirety.

FIELD OF THE INVENTION

The present invention relates to the use of L-Histidine and histidine derivatives for preventing Gadolinium Based Contrast Agent toxicity and free gadolinium ($Gd^{3+}$) accumulation in tissues, which might occur after the use of such CAs.

STATE OF THE ART

Clinical diagnosis has dramatically evolved in the last few decades, taking advantage from magnetic resonance Imaging (MRI).

Paramagnetic contrast media are injected intravenously to enhance the signal from water protons, thus allowing recognition of tissues with different water content.

Molecules used in contrast media have been shown to be remarkably safe in clinical use, but they still retain a degree of toxicity thought to be responsible of adverse reactions observed in a small percentage of patients (Membership of the Working Party, Guidelines Safety in magnetic Resonance units: an update, Anaesthesia, 2010, 65: 766-770).

One of the mechanism which has been proposed to explain the toxicity of paramagnetic gadolinium complexes used as contrast agents for the MRI is the in vivo dissociation and/or metabolism of the complex itself to yield metal and free ligands.

Both free ligands and metal were shown to possess a certain degree of toxicity, considered to be at least 20 times higher than that of their respective complexes, the free ligand by acting as a chelator of physiological positive ions ($Ca^{2+}$, $Zn^{2+}$) and the metal by taking place of those needed ions in body tissues, through a transmetallation process.

However, while the newly formed complexes are excreted by the urinary system, the metal typically accumulates in tissues, thus being a suitable indicator of complex dissociation.

In this regard, the in vivo stability of three gadolinium complexes used for MRI, MultiHance®, Omniscan® and Gadovist® has been further investigated in an animal model (rats) (S. Bussi et al. Exp. Toxicol. Pathol. 2007, 58: 323-330) and the pattern of gadolinium accumulation after release from the chelated compounds was estimated and compared to the one observed after administration of gadolinium acetate (free form) after single or repeated (3-weeks) administrations. Even though gadolinium release from chelated compounds has been confirmed unlikely to occur after a single injection of paramagnetic contrast media, used in this study at doses 10-fold higher than those recommended for diagnostic purposes, the highest gadolinium content due to complexed-Gd was observed in the kidneys, while spleen, femur and brain were mainly targeted by free gadolinium (mimicked by GdAc).

It's this aliquot of free Gadolinium released from GDBCA thought to be one of the causes of NSF (Nephrogenic Systemic Fibrosis) occurring to patients with renal insufficiency. NSF (see: "Gadolinium-based contrast agents (GBCAa) and the NSF risk: Regulatory update" Jan. 21, 2011, http://www-.fda.gov/downloads/AdvisoryCommittees/Committees-MeetingMaterials/Drugs/PeripheralandCentralNervous-SystemDrugsAdvisoryCommittee/UCM241072.pdf) was first recognized in 1997 in 15 dialyzed patients and described in 2000. This rare and highly debilitating disorder, that according to preclinical data has been attributed to an immunologic cascade triggered by free $Gd^{3+}$ (Canavese et al. J. Nephrol., 2008, 21:324-336) is characterized by an extensive thickening and hardening of the skin associated with skin-colored to erythematous papules that coalesce into erythematous to brawny plaques with a "peau d'orange" appearance. Nodules are sometimes also described. Joint contractures may develop, with patients progressively becoming wheelchair-dependent. Patients often complain of pruritus, causalgia and sharp pains. The distal extremities are the most common area of involvement (with a distribution from ankles to mid-thighs and from wrists to mid-upper arms), followed by the trunk. The lesions are typically symmetrical. It is worth noting that the face and neck are virtually never involved.

NSF can occur in all age-groups and there is no predilection for a geographic region, race or gender. So far, there is no recognized treatment for NSF. It has been suggested that improving renal function may slow down the development of the disease and, in some cases, may reverse its course. In 2006, two European teams independently suggested a link between the administration of gadolinium chelates used as contrast media for magnetic resonance imaging (MRI) and the occurrence of NSF in patients with renal failure. Numerous retrospective analyses rapidly followed and confirmed this temporal link (Broome D R, Eur. J. Radiol., 2008, 66:230-234). NSF has not been reported in patients with normal kidney function. Patients at greatest risk for developing NSF after receiving GBCAs are those with impaired elimination of the drug, including patients with acute kidney injury (AKI) or chronic, severe kidney disease (with a glomerular filtration rate or GFR<30 mL/min/1.73 $m^2$).

Policies to minimize the risk of NSF include the use of the lowest possible diagnostic dose and risk-benefit analysis prior of the administration of the GBCA (Altun E. et al. Acad. Radiol, 2009, 16: 897-905). Even though a straightforward link between free Gd and NSF has still not been clearly established, transmetallation may be considered as a promising starting point for studies aimed at further increasing safety in the field of MRI CA. Divalent ions such as Zinc and Copper are essential trace elements and are the necessary components of many enzymes. $Zn^{2+}$ and $Cu^{2+}$ ions are widely spread in animal cells and in blood. Due to their physicochemical affinity to the chelating moiety in GDBCA, these ions may promote transmetallation reactions with consequent release of free $Gd^{3+}$ in plasma.

The present invention and the new use of L-Histidine able to reduce the release of free gadolinium from GBDCA and its toxicity due to accumulation in target organs, might find an explanation by this mechanism.

L-Histidine is an amino acid: its use in human subjects has been described, even though with controversial results, for different purposes: as an anorectic agent i.e. in Schechter P J and Prakash J. Am. J. Clin. Nutrition 1979, 32:1011-1014 or as a hypocholesterolemic agent in Gerber DA et al. J. Am. J. Clin. Nutrition 1971, 1382-1383). Although a therapeutic effect has been observed in none of the cited references, after the administration of L-histidine up to 4 g/day, serum parameters including protein bound zinc (namely albumin and α2-macroglobulin bound zinc), serum and urinary zinc levels, monitored during the 15-days treatment, were not shown to be grossly altered. It's presently marketed as a food integrator and, accordingly, it's use is considered safe since a long time in human subjects. Although histidine-rich proteins are known to chelate divalent metal ions like $Zn^{2+}$ and $Cu^{2+}$, in vivo, this binding has been demonstrated to rely upon by their highly structured three-dimensional His-rich Zn-finger domains and in the cell, an extremely well compartmentalized environment.

Therefore the present use of L-Histidine and the therapeutic effects observed in vivo as shown in the present Application, should be considered quite unexpected.

SUMMARY OF THE INVENTION

It has been surprisingly found that L-histidine significantly reduces the release of free $Gd^{3+}$ from a Gadolinium Based Contrast Agent and the accumulation of free $Gd^{3+}$ into a patient's body, when administered together, or shortly before GDBCA administration.

Therefore according to a first aspect, the invention relates to L-Histidine or derivatives thereof for use in the prevention of a condition due to accumulation of Gadolinium ($Gd^{3+}$) in patient's target organs after a GDBCA (Gadolinium Based Contrast Agent) administration.

Said target organ is preferably selected from the group consisting of: bones, skin, blood, plasma and liver. The GDBCA is preferably selected from the group consisting of Gadoversetamide (OptiMark®), Gadodiamide (Omniscan®), Gadopentetate dimeglumine (Magnevist®), Gadoxetic acid and Gadoxetate disodium (Eovist®), Gadobutrol (Gadovist®), Gadofosfeset (Ablavar ®), Gadobenate dimeglumine (MultiHance), Gadoteridol (ProHance), Gadoteric acid (Dotarem®). Particularly preferred for co-administration with L-Histidine are linear ionic or non-ionic chelates, such as: Gadodiamide, Gadoversetamide, Gadopentetate dimeglumine, Gadobenate dimeglumine and Gadoxetic acid or Gadoxetate disodium.

Said condition is preferably a dermopathy, such as NSF (Nephrogenic systemic fibrosis), most preferably occurring in patients with renal function impairment, such as a chronic or acute renal disease, and with a reduced glomerular filtration rate, i.e. patients undergoing dialysis.

Cofactors, potentially influencing the development of a $Gd^{3+}$ induced dermopathy or NSF can be found in hypercalcemia, co-therapy with phosphate chelating agents (such as sevelamer HCl), acidosis, co-anti-hypertensive therapies and iron therapies.

According to a further aspect the invention relates to a kit of parts for administration of a GDBCA, comprising a first container with a composition wherein the active ingredient is L-Histidine or derivatives thereof and a container comprising a GDBCA, said kit for use in a method for the prevention of a condition due to accumulation of Gadolinium after a GDBCA administration.

Said composition comprising L-Histidine is preferably an oral composition for multiple or single dosage unit(s) of L-Histidine, preferably comprising, as a said single unit dose, an amount of 0.2-20 g L-Histidine or derivatives thereof.

DETAILED DESCRIPTION OF THE INVENTION

The invention is based on the effect of L-Histidine, preferably orally administered, on the release of free gadolinium after administration of a Gadolinium Based Contrast Agent (GDBCA).

By GDBCA are meant all contrast media based on Gadolinium and used generally for Contrast Enhanced Magnetic Resonance (CE-MR). Gadolinium, a paramagnetic metal in the lanthanide series, produces a large magnetic field that enhances the relaxation rates of water protons located close to the agent, thereby increasing signal intensity.

Since free $Gd^{3+}$ ions are toxic in vivo, in GDBCAs, the paramagnetic ion is chelated to create stable, inert, low molecular weight metal complexes.

Macrocyclic Gd chelates, such as Gadobutrol (GadoVist®, Bayer Shering Pharma AG), Gadoteridol (ProHance®, Bracco) and Gadoterate meglumine (Dotarem®, Guerbet) have a higher in vivo stability compared to linear $Gd^{3+}$ chelates, such as Gadoversetamide (OptiMark®), Gadodiamide (Gd-DTPA-BMA, OmniScan®), Gadopentetate dimeglumine (Gd-DTPA, Magnevist®, Bayer Shering Pharma AG) and gadobenate dimeglumine (MultiHance®, Bracco SpA). Gd based CA are rapidly cleared from intravascular spaces and eliminated from the human body mostly unchanged via (predominantly) renal excretion.

Chelated complexes are generally stable, although with different thermodynamic stability constants. Thermodynamic stability constant affinities have been described for the following GDBCAs: Gadoversetamide, Gadodiamide (Gd DTPA-BMA), Gadobutrol, Gd-DTPA, Gadofosveset-trisodium, Gadobenate dimeglumine (Gd-BOPTA), gadoxetic acid (EOB-DTPA), Gadoteridol (HP-DO3A) and Gd-DOTA (Caravan P. et al. Inorg. Chem, 2001: 40, 2170-2176).

One of the mechanisms which has been proposed to explain the somehow described toxicity of GDBCA, is their in vivo dissociation and/or metabolism of the complex itself, to yield free metal ($Gd^{3+}$) and ligand, through a process known as transmetallation (Morcos S K et al., Eur J. Radiol., 2008, 66: 175-179). These authors postulate that incidence of NSF (Nephrogenic Systemic Fibrosis) correlate with the stability of the $Gd^{3+}$-complexes being in fact more frequently associated with administration of Omniscan®, a linear non-ionic CA than ProHance® (a macrocyclic chelate).

Although transmetallation may, at least theoretically, affect a GDBCA in a way inversely proportional to the thermodynamic stability of the paramagnetic metal/chelate complex, this parameter does not sufficiently describe the factors affecting the in vivo transmetallation process (Tweedle et al. Magn Reson Imaging 1991; 9:409-415). Blood and, with the more reasons, living organisms are complex systems, where the presence of different ions and counter-ions in various concentrations and forms (free, bound to proteins or compartmentalized) influence the kinetics of the chelating reactions occurring in vivo. Indeed, also the kinetic stability of Gadolinium complexes is influenced by the presence of endogenous ions, counter-ions and other molecules in plasma. Citrate, i.e., a counter-ion physiologically present in the body, is known to form complexes with the $Gd^{3+}$ ions released in transmetallation reactions (G. E. Jackson, S. Wynchank, M. Woudenberg, *Magn. Reson. Med.*, 1990, 16, 57-66; L. Sarka, L. Burai, E. Brucher, *Chem. Eur. J.*, 2000, 6, 719-724) and, as described in more details in the experimental part, has been shown indeed to take part to the transmetallation reaction.

Transmetallation, where the free ligand may act as a chelator of endogenous positive ions ($Ca^{2+}$, $Zn^{2+}$, etc) with exchange of those ions in body tissues, generates in vivo free ligand and paramagnetic metal. Both species have been shown to possess a certain degree of acute toxicity, in terms of $LD_{50}$, at least 20 times higher than that of their respective complexes. However, while the newly formed complexes are excreted by the urinary system, $Gd^{3+}$ accumulates in tissues, with a well recognized toxicity, apparent in the skin and due to the triggering of an immune response to $Gd^{3+}$.

Bones have been shown to behave as natural repository for unchelated gadolinium (Wedeking P. & Tweedle, Nucl. Med. Biol., 1988, 15: 395-402), thus being a suitable indicator in the medium-long term time range of Gd-complex dissociation.

It has been postulated that mainly $Zn^{2+}$ could be involved in displacing significant amounts of gadolinium because the concentration of the former in blood is relatively high (55-125 µmol/L) (Vander et al., Invest Radiol 2001; 36:115-122), but even less abundant species may influence the affinity and the kinetics of the displacement reaction as shown in the plasma model selected.

Endogenous ions likely to compete with $Gd^{3+}$ are $Cu^{2+}$, $Ca^{2+}$, and $Zn^{2+}$. Among these, $Cu^{2+}$ is present in relatively small concentrations in the blood (1-10 µmol/L and $[Cu^{2+}]_{tot\ body}$=18 µmol/L: G. E. Jackson, S. Wynchank, M. Woudenberg, *Magn. Reson. Med.*, 1990, 16, 57-66), whereas $Ca^{2+}$ has relatively low affinity for organic ligands like DTPA and DTPA-BMA. Free Gadolinium release from GDBCA is thought to be one of the causes of NSF (Nephrogenic Systemic fibrosis) (Broome, 2008) in patients with renal failure (being the kidney, usually, the major excretory organ of GDBCA). Administration of histidine according to the present invention, which provides for the use of L-Histidine or derivatives thereof in the prevention of a condition due to accumulation of Gadolinium ($Gd^{3+}$) in a patient's target organs after a GDBCA (Gadolinium Based Contrast Agent) administration, allows a lower release of free gadolinium from GDBCA in vivo and its accumulation in tissues, particularly into the bones and the skin, thus decreasing the risks associated to its toxicity.

Zinc and Copper are essential trace elements, required for the functionality of many enzymes. Thus, $Zn^{2+}$ and $Cu^{2+}$ ions are widely spread in animal cells and in blood. Reduction of transmetallation between divalent ions, such as $Zn^{2+}$, $Cu^{2+}$ and $Gd^{3+}$ is believed to be at the basis of the reduction of gadolinium accumulation in tissues after GDBCA and L-Histidine administration according to the present invention. In fact, it has been experimentally confirmed that an increase in Histidine concentration from 0.2 to 0.8 mM in the presence of citrate can decrease the amount and the rate of exchange ligand formed with $Cu^{2+}$, for the Gd chelating moieties DTPA and DTPA-BMA, in a concentration dependent mode, in two different in vitro systems tested.

The toxic effects of metal deposition is known and generally acknowledged: it is partly prevented by adding excess amount of chelating compounds in the CA formulation itself: with the exception of MultiHance® and Dotarem®, in fact, all other contrast agents comprise an excess chelating compounds (up to 28.4 mg/ml in OptiMark®). However, free $Gd^{3+}$ is still released within the body before excretion of the complexes.

In this regard, the present invention which relates to pre- or co-administration of L-Histidine or derivatives thereof after GDBCA administration, in order to prevent $Gd^{3+}$ release and accumulation within the tissues, addresses the problem of toxicity due to paramagnetic metal accumulation after GDBCA administration.

The CA is preferably selected in the group consisting of ionic or non-ionic macrocyclic and linear Gd chelating agents, such as: Gadoversetamide (OptiMark®), Gadodiamide (Omniscan®), Gadopentetate dimeglumine (Magnevist®), Gadoxetic acid and Gadoxetate disodium (Eovist®), Gadobutrol (Gadovist®), Gadofosfeset (Ablavar ®), Gadobenate dimeglumine (MultiHance), Gadoteridol (ProHance), Gadoteric acid (Dotarem®). Particularly preferred for co-administration with L-Histidine are linear ionic or non-ionic chelates, such as: Gadodiamide, Gadoversetamide, Gadopentetate dimeglumine, Gadobenate dimeglumine and Gadoxetic acid or Gadoxetate disodium.

Preferably L-Histidine (or derivatives thereof) is administered at least 1 hour, more preferably 55' (min), 50', 45', 40', 35', 30', 25', 20', 15', 10' or 5 min before administration of the CA. At the latest, L-Histidine is co-administered together with the Contrast Agent. The optimal time for histidine administration, with respect to administration of the contrast agent, might more accurately be determined by calculating the relevant pharmacokinetic parameters, such as $C_{max}$, (peak concentration) $T_{max}$,(time to achieve maximum concentration), $t_{1/2\ \lambda Z}$ (half-life) or AUC in the dose range of interest. In particular $T_{max}$ should be considered for determining the optimal time for GBDCA administration after histidine administration. This parameter is preferably to be calculated for histidine derivatives, such as sustained release forms or polyhistidine complexes, the pharmacokinetic parameters of which might differ from L-Histidine or in case an alternative administration route is envisaged. In these cases, the time required to reach peak levels ($T_{max}$) of L-Histidine in serum after a single administration by the alternative route, or alternative histidine form, would allow better adapting the time for GBDCA administration.

By the oral route, it can be estimated that peak levels of L-Histidine administered in the salt form (HCl) are reached 30-45 min after oral administration (Sitton N G, Ann Rheum Dis, 1988, 47:48-52).

Since oral administration of L-Histidine in humans, up to 4-6 g/day, for several days, has been reported to provide neither important adverse effects nor minor inconveniences, its use up to gram doses is foreseen for the present invention as well, preferably in a single oral administration during a time closely prior to the administration of the GBDCA.

The possibility of an oral administration, a well known adsorption kinetic in man, and the high doses tolerated, represent important advantages for a preventive therapy with L-Histidine in GBDCA induced conditions for which, heavy toxic effects have until now only sporadically been reported. In general, in fact, it's very important for a preventive therapy neither interfering with the patient's general well being nor inducing discomfort.

In this regard, it should be mentioned that, although histidine can be administered also parenterally, a preferred administration is by os, before GDBCA, in order not to have the patient facing two injections within a short time from one another, instead of just one with the contrast agent. In fact, this may increase the patient's discomfort.

In contrast, oral administration of L-Histidine can be accomplished via a liquid solution comprising L-Histidine or derivatives thereof in a dose ranging from 10 to 200 mg/kg patient, not earlier than 60 min or preferably, from 45 to 15 min, or preferably 25-40 min before GBDCA administration, optionally together with or mixed within a liquid saline for hydration therapy.

Most common hydration mixtures come as powders to be mixed with water or an aqueous solution. Premixed solutions are also commercially available usually to be dissolved in 0.5-1 L of water to produce a solution containing (in mmol/L) Na 75-90, K 20, Cl 65-80, and optionally comprising citrate 5-15 and glucose 80-120. Histidine or derivatives thereof can be added to a hydration mix just before the addition of water.

As an alternative, histidine is administered as a solid composition, i.e. in tablets, together with water or hydration mixtures.

Target organs for free Gd accumulation based on experimental observations (S. Bussi et al., 2007), are generally considered the liver, spleen, bones and brain. According to the present invention a statistically significant decrease in free $Gd^{3+}$ deposition has been observed in bones (femur) and skin after administration of L-Histidine. These organs are indeed representative for an overall lower release of $Gd^{3+}$ from GBDCA in the presence of histidine or derivatives thereof. In particular, accumulation of $Gd^{3+}$ in the bones may be considered representative of the overall phenomenon, with a measure which is not affected by $Gd^{3+}$ fraction present in plasma, from which Gd it is very rapidly cleared, due to the scarce or null vascularisation in the bone tissue. Skin on its turn, represents the target organ for $Gd^{3+}$ deposition possibly leading to NSF, in kidney functionality impairment conditions.

A lower release of $Gd^{3+}$ from GBDCAs in the presence of L-Histidine has been confirmed by kinetic experimental data in a plasma model in vitro with either DTPA and DTPA-BMA, as better detailed in the experimental part.

Therefore the present invention relates to the still undisclosed use of L-Histidine or derivatives thereof for the prevention of metal accumulation, in particular $Gd^{3+}$, after GBDCA administration; accordingly, the present invention relates to L-Histidine and derivatives thereof for use in the preparation of a treatment preventing gadolinium deposition in target organs and, hence, for the preventing the toxic effect of this accumulation, in particular in the bones, spleen and skin.

Since metal accumulation, in particular free $Gd^{3+}$ has been accredited as a possible cause of NSF, in patients with impaired renal functions, the present invention also provides L-Histidine for use in a method aimed at the prevention of a condition due to Gd accumulation after GDBCA administration, in patients with kidney functionality impairment.

Said condition is preferably a dermopathy, such as NSF (Nephrogenic systemic fibrosis), most preferably occurring in patients with renal function impairment, such as a chronic or acute renal disease, and with a reduced glomerular filtration rate, i.e. in patients undergoing dialysis.

Cofactors, potentially influencing the development of a $Gd^{3+}$ induced dermopathy can be found in hypercalcemia, co-therapy with phosphate chelating agents (such as sevelamer HCl), acidosis, co-anti-hypertensive therapies and iron therapies.

In particular animal studies carried out in rats, have confirmed that a single oral pre-treatment of L-Histidine (administered at the dose of 4.38 mmol/kg, before administration of Omniscan®) is able to decrease significantly the $Gd^{3+}$ levels in the bones (femur) and skin, measured as nmol/gram of fresh tissue.

In particular, L-Histidine administration 30 min before Omniscan® administration induced a statistically significant decrease in $Gd^{3+}$ content in femur of about 40% (both as nmol/g fresh tissue and % ID) and in the skin. This data has been also confirmed by % Injected Dose at the bone level. It is known from the literature that bones and skin are the organs where the deposition of free gadolinium more frequently occurs (Bussi, 2007; Wedeking, 1988).

Histidine, is preferably L-Histidine, is administered as a powder of the di-hydrochloride or monohydrochloride salt either in the monohydrated as well as anhydrous form, preferably dissolved in an aqueous solution. The present invention also provides for L-Histidine as a poly-histidine complex or in any sustained or controlled release forms. Controlled release forms may comprise those described in US 2002/0004072.

When L-Histidine is administered orally, is preferably administered in a dose ranging from 10 to 200 mg/kg patient, not earlier than 60 min or preferably, from 45 min to 15 min, or preferably from 40 min to 25 min before GBDCA administration, optionally together with, or mixed within, a liquid saline for hydration therapy.

Even though oral administration is preferred because it's easier and usually well tolerated, L-Histidine can be administered by any other route, i.e. parenterally.

According to the data in the preclinical model and to the well established safety in humans, L-Histidine can be administered in humans up to 200 mg/kg/day. Thus, accordingly for human use, single dosage units comprise L-Histidine or salts derivatives in a quantity comprised from 0.2-20 g. Composition comprising L-Histidine or derivatives thereof for use in the prevention of metal ($Gd^{3+}$) accumulation in target organs due to a GDBCA administration are comprised within the preferred embodiments of the invention. Particularly preferred compositions are oral composition either liquid or solid wherein histidine or derivatives thereof is present in a quantity comprised from 0.2-20 g L-histidine hydrochloride per unit dose together with commonly used diluents (such as cellulose and derivatives thereof, polymethacrylates, starch and derivatives thereof, calcium carbonate or phosphate, alginates and derivatives), disintegrants (such as Na-croscarmellose), lubricants, excipients, stabilizers, flavourings and monovalent cationic salt integrators (see as a general review: "The handbook of pharmaceutical excipients" $4^{th}$ ed, 2003, Pharmaceutical Press, editors Raimond C. Rowe, Paul J. Sheskey, Paul J. Weller).

According to a preferred embodiment, the present invention also refers to a kit of parts for administration of a GDBCA, comprising a container with a composition wherein the active ingredient is L-Histidine or derivatives thereof and a container comprising a GDBCA.

The CA is preferably selected in the group consisting of ionic or non-ionic macrocyclic and linear Gd chelating agents, such as: Gadoversetamide (OptiMark®), Gadodiamide (Omniscan®), Gadopentetate dimeglumine (Magnevist®), Gadoxetic acid and Gadoxetate disodium (Eovist®), Gadobutrol (Gadovist®), Gadofosfeset (Ablavar ®), Gadobenate dimeglumine (MultiHance), Gadoteridol (ProHance), Gadoteric acid (Dotarem®). Particularly preferred for co-administration with L-Histidine are linear ionic or non-ionic chelates, such as: Gadodiamide, Gadoversetamide, Gadopentetate dimeglumine, Gadobenate dimeglumine and Gadoxetic acid or Gadoxetate disodium, and is optionally, but preferably present in a prefilled syringe.

Histidine, or preferably L-Histidine, is in the form of a powder or a tablet, ready for administration or to be dissolved before administration. Liquid compositions comprising L-histidine ready to use or to be prepared at the moment of administration, are acceptable according to the presently disclosed use.

According to a further embodiment the invention refers to a therapeutic method for preventing the toxic effect of Gadolinium accumulation into a patient's tissue, wherein said tissue is preferably selected from the group consisting of: bones, skin, spleen and blood, and/or to prevent NSF, which may occur after GBDCA administration in subjects, preferably in subjects with renal function impairment, which consists essentially in administering L-Histidine or derivatives thereof, preferably in a single unit oral dose, not earlier than 60' before GDBCA administration.

It follows that the invention also comprises a diagnostic method consisting essentially of L-Histidine or derivatives thereof administration, preferably in a single unit oral dose, followed by GBDCA administration within one hour period, even more preferably within 55 min 50 min 45 min 40 min 35 min 30 min 25 min 20 min and 15 min. More preferably the time range is comprised from 45 and 15 min or even, more preferably, from 40 to 20 min. GBDCA are preferably selected in the group consisting of ionic or non-ionic macrocyclic and linear Gd chelating agents, such as: Gadoversetamide (OptiMark®), Gadodiamide (Omniscan®), Gadopentetate dimeglumine (Magnevist®), Gadoxetic acid and Gadoxetate disodium (Eovist®), Gadobutrol (Gadovist®), Gadofosfeset (Ablavar ®), Gadobenate dimeglumine (MultiHance®), Gadoteridol (ProHance), Gadoteric acid (Dotarem®). Particularly preferred for co-administration with L-histidine are linear ionic or non-ionic chelates, such as: Gadodiamide, Gadoversetamide, Gadopentetate dimeglumine, Gadobenate dimeglumine and Gadoxetic acid or Gadoxetate disodium.

Unit dose may comprise L-Histidine or salts and derivatives for administering Histidine at a dose comprised from 0.2 to 20 g L-Histidine.

The following examples of the practice of the present invention are meant to be illustrative and are in no way limiting the scope of the invention.

EXPERIMENTAL PART

Example 1

Measurement of L-Histidine Levels in Plasma

Preparation of the Calibration Curve and Quality Control Samples.

Aliquots of L-Histidine dihydrochloride powder, accurately weighted, were transferred into 5 and 10 mL volumetric flasks. MilliQ-water was used to dissolve the powder. Standard solution was prepared to obtain CAL samples and CQ samples. The range of the stock standard solution was from 3.46 to 343 µg/mL. All standard solutions were stored at +4° C., in the dark: under these conditions they were considered stable for up to one month.

CAL samples were prepared by using the standard solution at the concentration of 3.46, 34.3, 68.6, 173 and 343 µg/mL and QC samples by using the standard solution at the concentration of 14.3, 67.1, 143 and 268 µg/mL.

CAL and QC samples were prepared by mixing 10 µL of Histidine standard solution with 90 ρL of blank rat plasma.

To these samples 20 µL of trichloroacetic acid (16% w/v) were added to precipitate the plasma proteins. The tubes were vortexed for few seconds and centrifuged for 10 min at 2000 g at room temperature; to 90 µL of the clear supernatant 45 µL of a soaked solution of Sodium carbonate (200 mM) and 90 µL of derivatizing solution (4 mg/mL of Dansyl chloride) were added. The tubes were vortexed for few seconds and incubated under stirring for 30 minutes at 60° C. Five microliters of Methylamine Hydrochloride were added and after cooling for 15 minutes, ten microliters of the sample were injected into the HPLC equipment.

Test plasma samples (S) were prepared by adding 10 µL of Milli-Q water to 90 µL of undiluted plasma or 90 µL of plasma suitably diluted with blank plasma (if sample volume was not enough). To these samples 20 µL of trichloroacetic acid (16% w/v) were added to precipitate the plasma proteins. The tubes were vortexed for few seconds and centrifuged for 10 min at 2000 g at room temperature; to 90 µL of the clear supernatant 45 µL of a soaked solution of Sodium carbonate (200 mM) and 90 µL of derivatizing solution (4 mg/mL of Dansyl chloride) were added. The tubes were vortexed for few seconds and incubated under stirring for 30 minutes at 60° C. Five microliters of Methylamine Hydrochloride were added and after cooling for 15 minutes, ten microliters of the sample were injected into the HPLC equipment. All plasma samples collected during the study were stored at −20° C. until analysis.

Results of HPLC analysis showed that it was possible to prepare a calibration curve for Histidine ranging from 3.46 to 343 µg/mL using a weighted linear regression. The goodness of the calibration curve and the performance of the chromatographic system complied to the defined acceptability criteria.

The precision of the back calculated concentrations of Histidine CAL standards (CV %) was 1.19% at 10.4 µg/mL, 1.25% at 41.3 µg/mL, 2.40% at 75.6 µg/mL, 2.81% at 180 µg/mL and 2.29% at 350 µg/mL.

The accuracy of the back calculated concentrations of Histidine CAL standards (ACC %) was −1.52% at 10.4 µg/mL, −3.25% at 41.3 µg/mL, 0.34% at 75.6 µg/mL, −1.57% at 180 µg/mL and −3.20% at 350 µg/mL.

The correlation coefficient value was 0.9993.

Histidine content in CAL and QC samples was the result of endogenous Histidine (concentration in blank plasma pool) and added Histidine (Calibration standards).

The precision of the back calculated concentrations of Histidine QC was between 85% and 115% for all the samples and considered acceptable.

The accuracy of the back calculated concentrations of Histidine QC was <15% for all the samples.

Precision of test samples was always acceptable.

Example 2

Experimental Design for Histidine Administration and Pharmacokinetic Studies

Animals
 Species and strain: CD(SD)IGS BR rat
 sex of animals: males
 Weight and age at treatment: 306-376 g (10-14 weeks old)
 Supplier: Charles River Laboratories, Calco (LC), Italy
 All the procedures involving the animals were conducted according to the national and international laws on experimental animal (L.D. 116/92; C.D. EEC 86/609; C.R. 2007/526/EC). No validated non animal alternatives are known to meet the objectives of the study.

Rats were used to determine the pharmacokinetic parameters after administration of three different histidine doses (100, 500 and 1000 mg/kg, three animals for each group).

Three animals were used for blank plasma sample collection for the calibration curve.

Statistical Analysis

Plasma concentrations of Histidine as a function of time after injection C(t), were analyzed by non-parametric methods using the computer program WIN-NONLIN 4.0.1. For the tested doses, a non-compartmental analysis was performed using the average plasma concentrations from 3 animals for each time point (except when indicated). For Cmax (peak plasma concentration) and the corresponding tmax (amount of time that a drug is present at Cmax in plasma) the observed values were reported. The terminal phase elimination rate constant ($\lambda z$) was estimated by log-linear regression of those data points visually assessed to be in the terminal phase of the profile. At least three terminal plasma concentrations were used for estimating $\lambda z$. The terminal elimination half life (t ½ $\lambda z$, time required for a drug to decline to half of its original plasma value) was calculated as t ½ $\lambda z$=ln 2/$\lambda z$. Area under the plasma concentration-time curve to the last observable plasma concentration (AUC(0 to t)) was calculated from observed data using the logarithmic trapezoidal method. Total area under the plasma concentration-time curve from zero to infinity (AUC(0 to $\infty$)) was estimated by AUC(0 to $\infty$) =AUC(0 to t) +ct/$\lambda z$, where ct is the predicted concentration at the last quantified time point. AUC defines extent of drug exposure.

Histidine basal values in rat plasma ranged from 4.60 to 8.39 μg/mL.

Cmax values of 9.0, 20.9 and 36.0 μg/mL were obtained 30 min, 1 h and 30 min (tmax) after oral administration at 100, 500, 1000 mg/kg, respectively. The half life values associated with the terminal elimination phase t ½ $\lambda z$ were 51, 47 and 13 minutes for animals treated at the three different doses, respectively (see Table A). These values suggest a slightly faster elimination from plasma for the highest dose.

The AUC(0 to $\infty$) values were 0.55, 0.63 and 0.39 h*mg/mL, respectively. The values were similar indicating a similar systemic exposure at the different doses. Moreover, they were in the range of the AUC(0 to $\infty$) value (0.477 h*mg/mL) found in healthy volunteers after a single oral administration of Histidine at 100 mg/kg (Sitton N G, Ann Rheum Dis, 1988, 47:48-52).

The total plasma clearance values were 180, 790 and 2562 mL/h/kg for the three doses, respectively. Clearance values increased with increasing the dose.

TABLE A

Pharmacokinetic values

| Parameters | Units | Histidine mg/kg (mmol/kg) | | |
|---|---|---|---|---|
| | | 100 (0.438) | 500 (2.192) | 1000 (4.38) |
| $C_{max}$ | μg/mL | 9.0 | 20.9 | 36.0 |
| $t_{max}$ | h | 0.5 | 1 | 0.5 |
| $t_{1/2}\lambda_z$ | h | 51 | 47 | 13 |
| $AUC_{(0\ to\ \infty)}$ | h * mg/mL | 0.55 | 0.63 | 0.39 |

$C_{max}$ values increased with increasing the dose. $T_{max}$ was calculated twice 30 min (or 1 h); AUC(0 to inf) were similar at the three doses. No clinical signs were observed up to 1000 mg/kg, indicating that the compound is well tolerated up to 5 times the highest dose foreseen for patients (200 mg/kg).

Example 3

Administration of L-Histidine and Measure of $Gd^{3+}$ Target Organ Accumulation Animals:
Rat Sprague Dawley
sex of animals: males
Weight and age at treatment: 208-233 g, 7 weeks old
Supplier: Charles River Laboratories, Calco (LC), Italy
A period of at least 3 days was allowed between animal arrival and allocation to treatment groups.

Three animals were used in order to collect blank plasma samples for the calibration curve.

L-Histidine was orally administered by gavage, while Omniscan® was intravenously administered.

Histidine was administered 30 min before Ominiscan® administration at a dose of 4.38 mmol/kg; Omniscan® (Gd (DTPA-BMA), at a dose of 1 mM/kg, was administered via the tail vein at an injection rate of 2 mL/min with an Harvard infusion pump. Histidine and Ominscan® were administered at room temperature. Animals were sacrificed 24 h after Omniscan® administration, and their organs were collected for ICP-MS gadolinium content determination.

Mortality and Clinical Signs

On the day of treatment animals were observed before treatment and at least once after dosing, to detect any clinical signs or reaction to treatment. Severity, time of onset, duration of toxic signs and mortality were recorded, if any.

Gross Pathology Examination

On the day of scheduled sacrifice, animals were anesthetized with an inhalation agent, sevoflurane, at an respiratory concentration of 3% in induction and 1-2% in maintenance and bled after collection of blood from the abdominal aorta. After exsanguination, liver, spleen, femur and skin of all animals were excised, weighed and prepared for ICP-MS determination of gadolinium content. Sample digestion (spleen and femur) was performed by a microwave system (MARS-5 CEM Corporation).

Liver and skin samples were freeze-dried with a lyophilizer (Alpha-1-2LD Plus, CHRIST) after being frozen at $-80°$ C. for at least 1 h. After drying, dehydrated livers were weighed and then ground in a mortar. An amount of 0.3 g of the dried ground liver was accurately weighed and suspended in 1.0 mL of nitric acid (65% w/w). This solution was stored at 2-8° C. for at least 12 h. ICP-MS assay for gadolinium in biological samples (Bussi, 2007) was carried out on an ELAN 6100 Perkin Elmer Spectrometer, operating with the following instrumental parameters:

Nebulizer flow: 0.95-0.98 L/min
Argon auxiliary gas flow: 0.2 L/min
Argon plasma gas flow: 15 L/min
Argon pressure (auxiliary, nebulizer, plasma): 7.5 atm
RF power: 1250 W
Pump flow rate: 1.5 mL/min
Atomic Mass: 156.934 amu
Waiting start-up time: 45 min Data Analysis Gadolinium content in organs was reported as μg of Gd. Data were transformed into nmol/g tissue (Table B) and percent of injected dose (% ID, Table C) according to the following calculation:

$$nmol/g \text{ of fresh tissue} = \frac{\text{Gadolinium content } (\mu g) \times 1000}{157.25 \times \text{fresh organ weight}(g)}$$

$$\% \text{ } ID = \frac{100 \times \text{Gadolinium content} (\mu g)}{\text{Dose } (\mu mol/g) \times \text{animal weight } (g) \times 157.25}$$

Statistical analysis was performed on nmol/g tissue and percent of injected dose (% ID) by applying the One-Way ANOVA test, followed by post-hoc Dunnett's test or the non-parametric Kruskal-Wallis test, followed by Mann-Whitney U test, when the data did not meet the assumptions of ANOVA.

Results

No mortalities nor changes in clinical signs were observed both after histidine and Omniscan® administration. No macroscopic changes were observed at necropsy.

In liver and spleen no significant changes in $Gd^{3+}$ content were noted in groups 2 and 3 (histidine pretreatment at 30 min and 1 h, respectively) in comparison to group 1 (no histidine pretreatment).

$Gd^{3+}$ content in skin showed a statistically significant decrease (p<0.05) in group 2 (histidine pretreatment at 30 min), in comparison to group 1 (no histidine pretreatment). Values of 11.25 and 16.1 nmol/g tissue were assessed, respectively (Table B).

Gadolinium content in femur showed a statistically significant decrease (p<0.01) in group 2 (histidine pretreatment at 30 min), in comparison to group 1 (no histidine pretreatment). The decrease was around 40% (6.90 nmol/g tissue versus 10.9 nmol/g tissue). This effect was also observed in % ID at the same significance level.

The % ID in liver, spleen and skin was not significantly different in group 2 (histidine pretreatment at 30 min) in comparison to group 1 (no histidine pretreatment) (Table C).

However the % ID in femur showed a statistically significant decrease (p<0.01) in group 2 (histidine pretreatment at 30 min), in comparison to group 1 (no histidine pretreatment). A decrease of about 40% was observed (0.00166% ID versus 0.00295% ID).

TABLE B

Gadolinium content in spleen, femour, skin and liver (nmol/g of tissue, mean values and SD)

| Group | Omniscan® (mmol/kg) | Histidine pre-treatment | | Gadolinium content (nmol/g of tissue) | | | |
|---|---|---|---|---|---|---|---|
| | | | | spleen | femour | skin | liver |
| 1 N = 5 | 1 | / | Mean SD N | 22.6 (2.0) 5 | 10.9 (1.7) 5 | 16.1 (2.4) 5 | 21.1 (2.9) 5 |
| 2 N = 5 | 1 | 30 min | Mean SD N | 20.0 (3.2) 5 | 6.90** (0.52) 5 | 11.25* (0.92) 4 | 20.7 (1.8) 5 |

**p < 0.01;
*p < 0.05

TABLE C

% ID in spleen, femour, skin and liver (mean values and SD).

| Group | Omniscan® (mmol/kg) | Histidine pre-treatment | | % ID | | | |
|---|---|---|---|---|---|---|---|
| | | | | spleen | femour | skin | liver |
| 1 | 1 | / | Mean SD N | 0.00540 (0.00060) 5 | 0.00295 (0.00048) 5 | 0.0060 (0.0016) 5 | 0.110 (0.018) 5 |
| 2 | 1 | 30 min | Mean SD N | 0.00478 (0.00095) 5 | 0.00166** (0.00010) 5 | 0.0067 (0.0015) 4 | 0.1094 (0.0062) 5 |

**p < 0.01

Histidine treatment 60 min before Omniscan® administration didn't show, in this model, any effect on $Gd^{3+}$ accumulation. This result is consistent with the observed $T_{max}$ of L-Histidine (see Example 1: $T_{max}$ at 100 and 1000 mg/kg=0.5 h)

A statistically significant decrease in $Gd^{3+}$ content in femour of about 40% (both as nmol/g tissue and % ID) was observed in animals treated with histidine 30 min before Omniscan® administration. A decrease in the total content of Gd was observed in the skin (Table B, p 0.05).

In conclusion, $Gd^{3+}$ levels in rat femur decreased (40% less) after a single oral pretreatment with histidine (at the dose of 4.38 mmol/kg) administered 30 min before the intravenous administration of Omniscan® at the dose of 1 mmol/kg.

Example 4

Kinetics of the Transmetallation Reactions of the Gd(DTPA), and Gd(DTPA-BMA) Complexes with a Divalent Ion [Cu(II)] in the Presence of Citrate and Histidine In order to have some clues on the kinetics of a possible transmetallation reactions in the presence of citrate (an important counter-ion present in plasma and found to be highly interactive with $Gd^{3+}$) and increasing amounts of histidine, the rates of the following reactions have been studied:

$$GdL+Cu^{2+}+His+cit \rightleftharpoons CuL+Gd(cit)+His \quad (1)$$

In the experiment, the concentration used for $Gd^{3+}$ complex (GdL), citrate and $Cu^{2+}$ were: 2.0, 2.0 and 0.1 mM, respectively, while the concentration of His was varied (0.2, 0.4, 0.6 and 0.8 mM).

Figure 1:
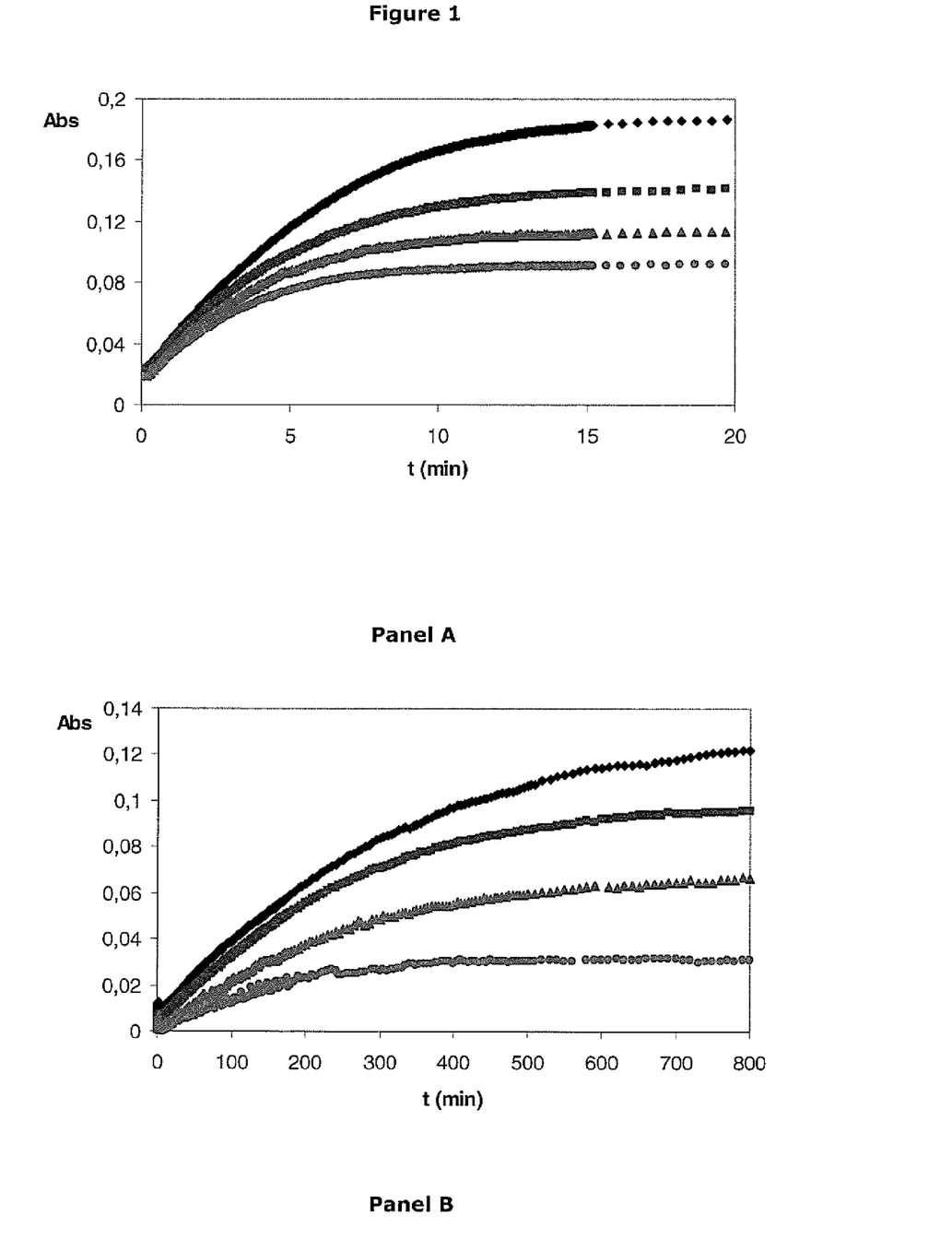
FIG. 1. Absorbance values as a function of time in the reaction of Gd(DTPA-BMA) (panel A) and Gd(DTPA) (panel B) with Cu(II) in the presence of citrate and L-Histidine in concentration of: 0.2 (black line, ♦), 0.4 (dark gray, ■), 0.6 (gray, ▲) and 0.8 (light gray, ●) mM ([GdL]=2.0 mM, [Cu]=0.1 mM, [cit]=2.0 mM, [His]=0.2-0.4-0.6-0.8 mM, [HEPES]=0.01 M, pH=7.0, 25° C., 0.15 M NaCl).

The progress of the exchange reactions (1) has been studied by spectrophotometry (Cary 1E spectrophotometer) at 300 nm, with the use of 1.0 cm quartz cell at 25° C. in 0.15 M NaCl in the pH range 6-8. The experimental data (absorbance values) obtained for the reaction of Gd(DTPA-BMA) and Gd(DTPA) in the presence of $Cu^{2+}$, histidine and citrate are shown in FIG. 1.

The progress of the transmetallation reactions (1) results in the increase of the absorbance values because of the formation of CuL complexes. The data in FIG. 1 clearly show that the increase of histidine concentration has two effects: a) a decrease of the reaction rates (initial part of the curves) and b) more importantly, the extent of the conversions in the reactions (1) the saturation concentrations of CuL complexes significantly decreases. In other words, in the presence of histidine, both the rates and the extent of the transmetallation reactions occurring between the Gd-containing open-chain MRI contrast agents and the endogenous $Cu^{2+}$ significantly decrease, which in this model, decreases the amount of $Gd^{3+}$, as Gd-cit specie in the reaction (1), corresponding to Gd available for exchange with body fluids.

Example 5

Dissociation of the Gd(DTPA-BMA) Complex in Artificial Plasma in the Presence of Histidine Excess The following composition of artificial plasma according to a simplified plasma model (P. M. May, P. W. Linder, D. R. Williams, *J. Chem. Soc. Dalton Trans.*, 1977, 588-595) was prepared:

| | | |
|---|---|---|
| 0.025M $NaHCO_3$ | 2.5 mM $CaCl_2$ | 55 μM Asp |
| 0.11 mM $Na_3Cit$ | 16 μM $ZnCl_2$ | 48 μM Glu |
| 1.0 mM $Na_2HPO_4$ | 18 μM $CuCl_2$ | 178 μM Lys |
| 0.15M NaCl | 85 μM L-His | 0.7 mM HSA |
| 0.01M HEPES | 23 μM Cys | |

1.0 mM Omniscan (Gd(DTPA-BMA)) was added to the solution and relaxivity values measured at 20 MHz with a Bruker Minispec MQ20 instrument at pH=7.5 and 37° C.

Figure 2:
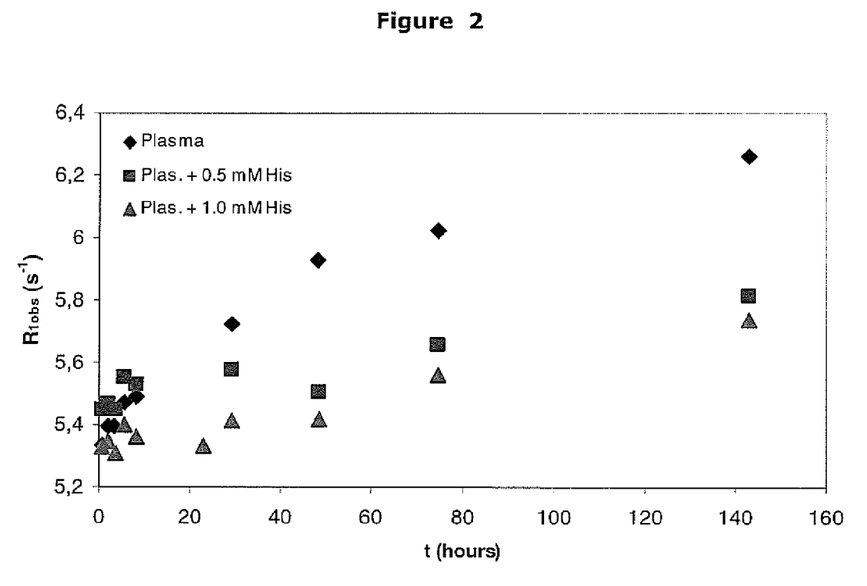
FIG. 2. Relaxivity values as a function of time for the decomplexation reaction of Gd(DTPA-BMA) (GdL) in artificial plasma ([GdL]=1.0 mM, [His]=0.5 or 1.0 mM, pH=7.5, 37° C., 0.15 M NaCl). Artificial plasma (♦), comprising 0.5 mM His (■) or 1 mM His (▲).

As shown in FIG. 2, relaxivity values increase as a function of time, indicating the dissociation of Gd(DTPA-BMA). As observed in FIG. 2, the relaxivity values of Gd(DTPA-BMA) (Omniscan) in blood serum significantly increase with elapsing time, which was explained by the dissociation of the complex and interaction of "free" $Gd^{3+}$ with some components of the artificial plasma model. The addition of histidine to the sample (0.5 mM and 1.0 mM) resulted in a concentration dependent drop in the increase of the relaxivity values, probably due to the shift of the equilibria to the formation of highly stable $Cu(His)_2$ and $Zn(His)_2$ complexes and the absence of the transmetallation reactions between the Gd(DTPA-BMA) and $Cu(His)_2$ or $Zn(His)_2$. Therefore the presence of histidine is beneficial for the stability of the $Gd^{3+}$complex in this model.

Figure 3:
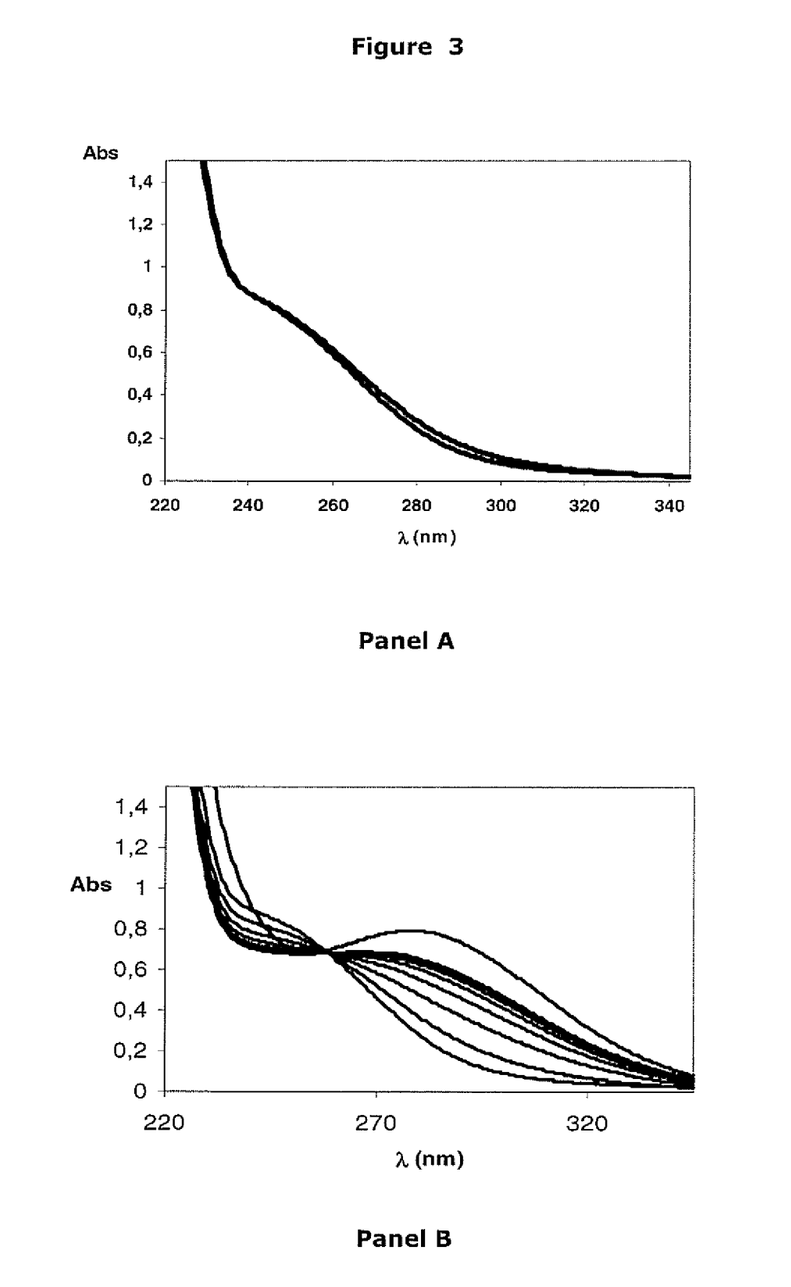
FIG. 3. The UV spectrum of $Cu(His)_2$ in the presence of Gd(DTPA-BMA) excess (Panel A) and in the presence of citrate and Gd(DTPA-BMA) excess (Panel B). ($Cu(His)_2$=0.2 mM, Gd(DTPA-BMA)=2.0 mM) (A). ($Cu(His)_2$=0.2 mM, Gd(DTPA-BMA)=2.0 mM, Citrate=2.0 mM) (B). pH=6.5, 25° C., 0.15 M NaCl.

It is possible to conclude that in body fluids transmetallation reactions may take place between the DTPA-derivative $Gd^{3+}$ complexes and endogenous metal ions, like $Cu^{2+}$ and $Zn^{2+}$. The possibility of the transmetallation reactions can be predicted on the basis of the stability constants of complexes formed between the most important endogenous metals and ligands. The stability constants have been determined for the $Gd^{3+}$, $Cu^{2+}$ and $Zn^{2+}$ complexes of the DTPA, DTPA-BMA, citrate and histidine ligands. The species distribution calculations based on the stability data indicate the importance of the citrate ion in transmetallation reactions, which may take place in the presence of citrate. The species distribution calculations have been experimentally verified by following the exchange reactions between Gd(DTPA-BMA) and $Cu(His)_2$ in the absence and presence of citrate. In FIG. 3A the spectrum of $Cu(His)_2$ shows no changes in the presence of Gd(DTPA-BMA) excess. However, when citrate is also present, the changes in the spectra indicate the formation of Cu(DTPA-BMA), indicating that the transmetallation reaction takes place (FIG. 3B).

The addition of histidine (L-Histidine) generally reduces the extent of the conversion of the transmetallation reactions. The results of the kinetic studies between the $Gd^{3+}$ complexes and $Cu^{2+}$ show that both the rates and the conversion of the transmetallation reactions decrease with increasing concentration of histidine. The studies on the relaxivity values of the Gd(DTPA-BMA) in an artificial serum model also indicate that the extent of dissociation of the $Gd^{3+}$ complex significantly decreases in the presence of increasing concentration of histidine.

The invention claimed is:

1. A method of preventing Gadolinium ($Gd^{3+}$) accumulation in a patient's target organ after a GDBCA (Gadolinium Based Contrast Agent) administration comprising: administering L-Histidine or a derivative thereof before or simultaneous with administration of a GDBCA (Gadolinium Based Contrast Agent).

2. The method according to claim 1, wherein said L-Histidine derivative is selected from the group consisting of: L-Histidine di-hydrochloride, L-Histidine monohydrochloride monohydrate.

3. The method according to claim 1, wherein said target organ is selected from the group consisting of: bones, skin, blood, plasma and liver.

4. The method according to claim 1, wherein said GDBCA is an ionic or non-ionic macrocyclic or linear Gd chelating agent selected from the group consisting of: Gadoversetamide, Gadodiamide, Gadopentetate dimeglumine, Gadoxetic acid, Gadoxetate disodium, Gadobutrol, Gadofosfeset, Gadobenate dimeglumine, Gadoteridol, and Gadoteric acid.

5. The method according to claim 4, wherein said GDBCA is selected from the group consisting of: Gadodiamide, Gadoversetamide, Gadopentetate dimeglumine, Gadobenate dimeglumine and Gadoxetic acid and Gadoxetate disodium.

6. A method for the prevention of a condition associated with accumulation of Gadolinium ($Gd^{3+}$) in patient's target organs after administration of a GDBCA (Gadolinium Based Contrast Agent) selected from the group consisting of dermopathy and NSF (Nephrogenic Systemic Fibrosis), comprising administration of a composition comprising L-Histidine or derivatives thereof prior to or simultaneous with administration of the GDBCA.

7. The method according to claim 6, wherein the composition comprises 0.2-20 g/L-Histidine.

8. The method according to claim 6, wherein the patient has impaired renal function.

9. A kit of parts for administration of a GDBCA, comprising a first container comprising a composition wherein the active ingredient is L-Histidine or a derivative thereof and a second container comprising a GDBCA.

10. The kit of parts according to claim 9, wherein said GDBCA is selected from the group consisting of: Gadoversetamide, Gadodiamide, Gadopentetate dimeglumine, Gadoxetic acid, Gadoxetate disodium, Gadobutrol, Gadofosfeset, Gadobenate dimeglumine, Gadoteridol, and Gadoteric acid.

11. The kit of parts according to any one of claims 9-10, wherein the GDBCA is comprised in a prefilled syringe.

12. The kit of parts according to claim 11, wherein said composition is an oral composition comprising multiple or single dosage unit(s) of L-Histidine.

13. The kit of parts according to claim 12, wherein said single unit dose comprises 0.2-20 g L-Histidine or derivatives thereof.

* * * * *